United States Patent [19]
Kajino et al.

[11] Patent Number: 5,125,409
[45] Date of Patent: Jun. 30, 1992

[54] ULTRASONIC DIAGNOSTIC APPARATUS AND METHOD FOR OPHTHALMOLOGY

[75] Inventors: Tadashi Kajino, Okazaki; Munehiro Nakao, Toyokawa, both of Japan

[73] Assignee: Nidek Co., Ltd., Gamagori, Japan

[21] Appl. No.: 664,691

[22] Filed: Mar. 5, 1991

[51] Int. Cl.⁵ .............................................. A61B 8/00
[52] U.S. Cl. ......................... 128/660.07; 128/661.06; 128/649
[58] Field of Search ...... 128/660.07, 661.06, 128/676, 649, 652, 419 R, 419 PT

[56] References Cited

U.S. PATENT DOCUMENTS

| | | | |
|---|---|---|---|
| 3,934,462 | 1/1976 | Rende | 128/652 |
| 4,564,018 | 1/1986 | Hutchison et al. | 128/661.06 |
| 4,809,697 | 3/1989 | Causey et al. | 128/419 PT |
| 5,012,808 | 5/1991 | Stubbers et al. | 128/419 R |
| 5,029,587 | 7/1991 | Baba et al. | 128/661.06 |

Primary Examiner—Francis Jaworski
Assistant Examiner—George Manuel
Attorney, Agent, or Firm—Armstrong, Nikaido, Marmelstein, Kubovcik and Murray

[57] ABSTRACT

An ultrasonic diagnostic apparatus for ophthalmology according to the present invention includes a card connector into and from which a memory card is to be inserted and removed, a microcomputer incorporated in the apparatus, and a card interface for data transfer between the memory card and the microcomputer therethrough. Diagnosis data is obtained based on data of the memory card and data in the microcomputer, whereby even when a new program or data necessary for diagnosis is developed, the apparatus can immediately used the new program or data while eliminating the need for being modified. The apparatus thus can readily reproduce patient data and efficiently diagnose many patients.

6 Claims, 5 Drawing Sheets

F I G. 1
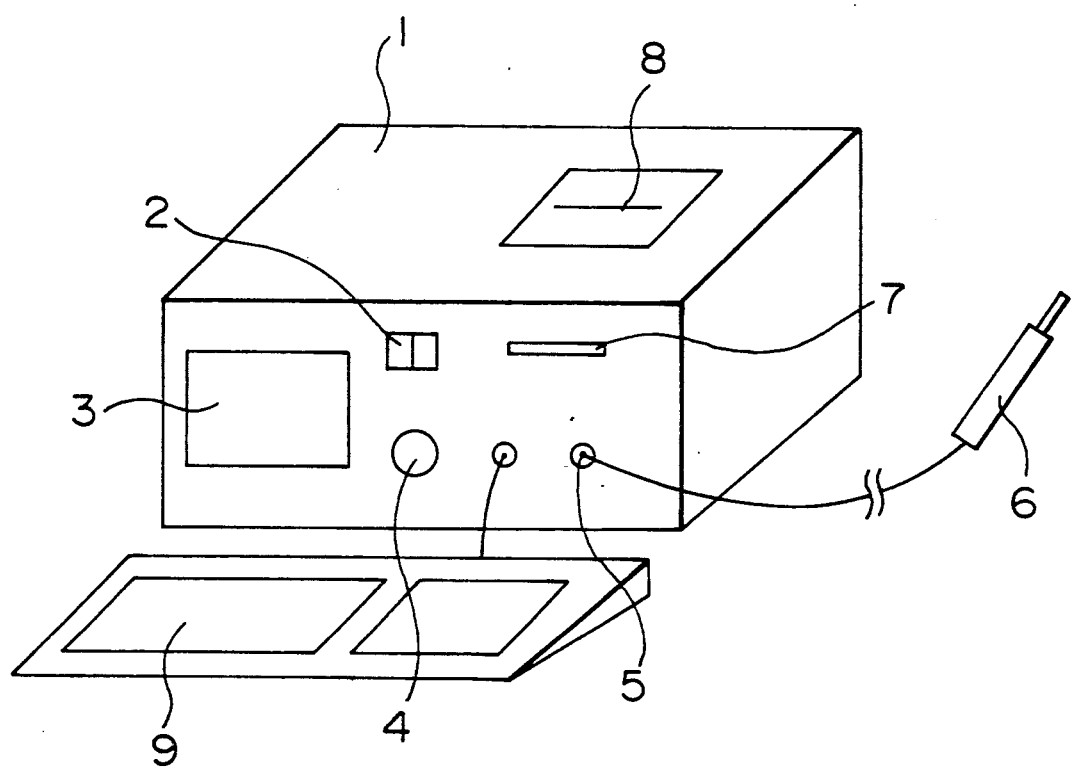

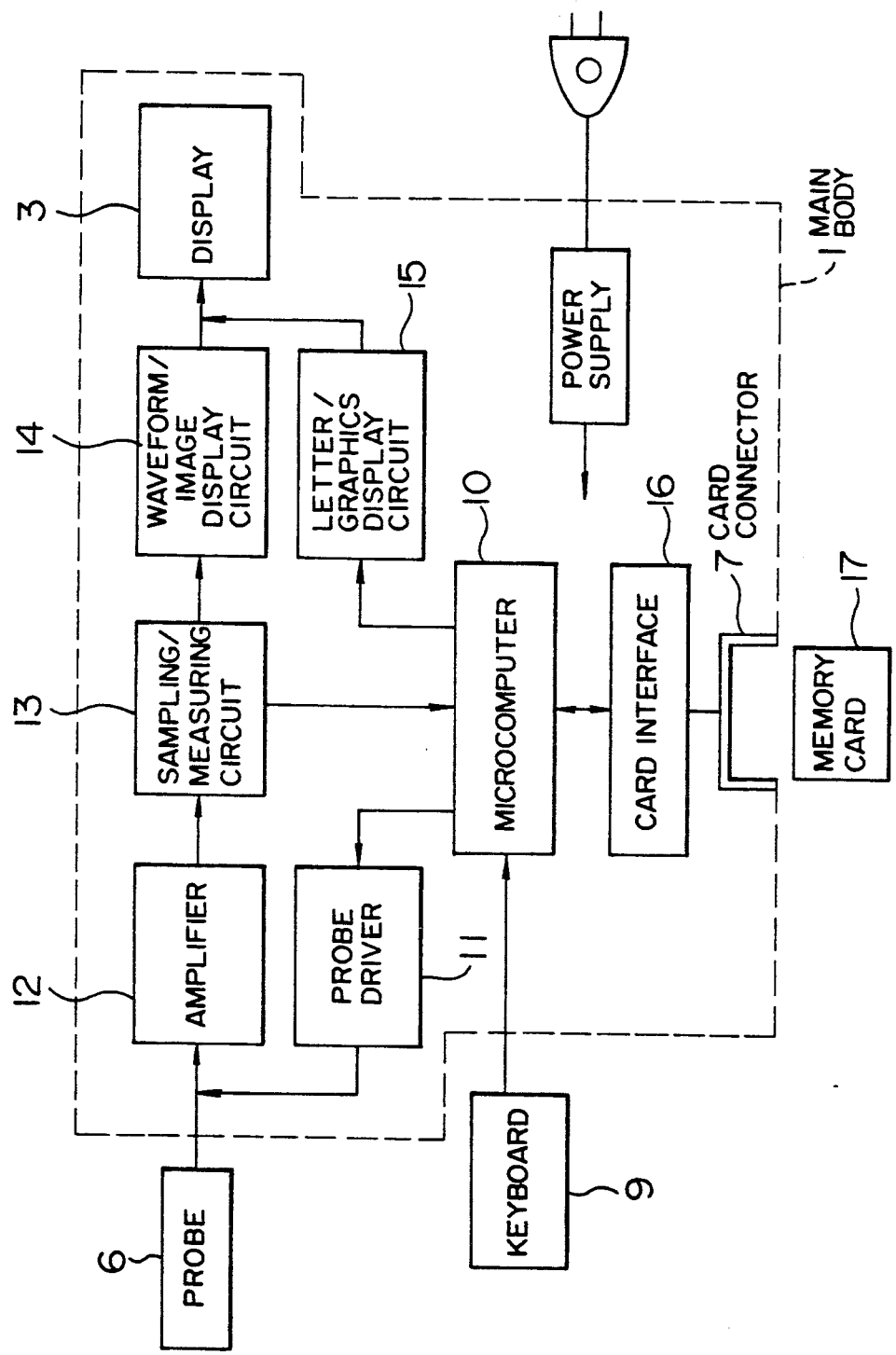
F I G. 2

ULTRASONIC DIAGNOSTIC APPARATUS AND METHOD FOR OPHTHALMOLOGY

BACKGROUND OF THE INVENTION

The present invention generally relates to ultrasonic diagnostic apparatuses for ophthalmology and more particularly, to an ultrasonic diagnostic apparatus and method for ophthalmology which use ultrasonic waves suitably for measurement of the axial length and for diagnosis of the intraocular tissue.

When comparison is made between diagnostic apparatuses for ophthalmology and medical ultrasonic diagnostic apparatuses for applications other than ophthalmology (such latter apparatuses are sometimes referred to merely as the non-ophthalmic apparatuses), the ophthalmic apparatuses require probes to be contacted with the eye to be examined. For that reason, the structure and arrangement of the probes are devised in various ways but how ophthalmic apparatuses transmit and receive ultrasonic waves is not especially different from how non-ophthalmic apparatuses operate. In ultrasonic diagnostic apparatuses for ophthalmology, it is not very helpful to only receive the ultrasonic waves reflected by the respective intraocular tissue, process the received ultrasonic signal by a known processing technique, and then indicate the signal on a display in the form of an A-mode waveform or a B-mode image. It is when the measurement data thus obtained is added to the data base on the ophthalmologist's experience that the measurement data can become helpful. of an intraocular iens (an "IOL") inserted after cataract surgery. The calculation of IOL power is carried out by substituting into a power calculation formula the axial length obtained by the ultrasonic diagnostic apparatus. Such IOL power calculations have been formulated based on the ophthalmologist's long-term experience; there now exist 5 such typical formulas. Each of these formulas has merits and demerits. In this way, no single IOL power calculation formula has yet been recognized by a majority of ophthalmologists for its validity. Since the existing formulas have been established based on the individual ophthalmologist's experiences, the formulas tend to vary as the individual opthalmologist's experience is added thereto.

The same applicant as the present application has proposed an ultrasonic diagnostic apparatus for ophthalmology suitable for differential diagnostics in U.S. patent application Ser. No. 313,203 filed on Feb. 21, 1989. This apparatus comprising a means for storing therein a plurality of reflected-echo images having a dynamic range larger than a display image is arranged to retrieve an image of a given condition, which corresponds to the obtained image by adjusting its dynamic range, from the reflection echo images stored in said means. Even in this apparatus, it is impossible to determine what condition is proper for retrieving an image from the storage memory. In other words, the individual ophthalmologist's continual clinical experience is heavily relied upon in using the apparatus for diagnosis, and must be dependable.

In conventional ultrasonic diagnostic apparatuses for ophthalmology, data necessary for various sorts of processings for calculating IOL power, etc. has been stored only in a memory incorporated in a main body. Thus, whenever a new program and its data necessary for diagnostics (e.g., a new IOL power calculation formula) are published, the memory of the main body having the old program and data must be with considerable time and effort changed to substitute in the new program and/or data.

In this way, the operating life of the above prior art apparatus is the same as that of the program and data stored in memory of the main body. However, now that many researchers actively and frequently publish their research results within a short time, it is inconvenient and disadvantageous that the lifespan of the apparatus is influenced directly by the lifespan of the built-in program and data.

Further, with the prior art apparatus having such a disadvantage that, since measured and diagnosed results cannot be stored, an operator cannot measure the next patient until he or she finishes a series of processings and diagnosis with regard to the current patient. This results in other patients being undesirably kept waiting. This also leads to the fact that the ophthalmologist cannot readily make a series of progress examinations because the past measured and diagnosed results of the patients cannot be reproduced in the apparatus. Furthermore, once a diagnosis is finished, the diagnosed results are preserved only in the form of data printed on a paper sheet. Accordingly, when it is desired to use a new program or data, the examination must desirably be restarted from the beginning. In addition, even when the above apparatuses are arranged so as to store diagnosed results therein to some extent, each storage capacity within the apparatuses has its limit. The provision of disk or a large capacity memory built in the apparatus leads unfavorably to the large size and high cost of the apparatus.

SUMMARY OF THE INVENTION

It is an object of the present invention to provide an ultrasonic diagnostic apparatus and method for ophthalmology which, even when a new program or data necessary for diagnosis is developed, can immediately use the new program or data without being subjected to any modification of its structure.

Another object of the present invention is to provide an ultrasonic diagnostic apparatus and method for ophthalmology which can readily produce data on a patient such that the patient can be diagnosed based o a new program or data.

A further object of the present invention is to provide an ultrasonic diagnostic apparatus and method for ophthalmology by which many patients can be diagnosed efficiently.

The above objects can be attained by providing an ultrasonic diagnostic apparatus and method for ophthalmology which have the following features (1) to (5):

(1) In an ultrasonic apparatus for ophthalmology transmitting and receiving ultrasonic waves and for outputting a plurality of ultrasonic reflection echo images therefrom, the apparatus includes a card connector into and from which a memory card is to be inserted and removed, a microcomputer incorporated in the apparatus, and a card interface for daft transfer between the memory card and the microcomputer therethrough, wherein the diagnosis data is obtained on the basis of both data of the memory card and data of the microcomputer.

(2) The data of the memory card includes a new program and processing data necessary for diagnosis.

(3) The data of the memory card is temporarily or permanently stored in the microcomputer.

(4) If the data of the memory card is temporarily stored in the microcomputer, data of another memory card can be read out and/or written.

(5) The data of the memory card includes measurement data specific to individual patients.

BRIEF DESCRIPTION OF THE DRAWINGS

FIG. 1 is a perspective view showing an ultrasonic diagnostic apparatus for ophthalmology in accordance with an embodiment of the present invention;

FIG. 2 is a block diagram of a schematic arrangement of the embodiment apparatus;

DESCRIPTION OF THE PREFERRED EMBODIMENTS

Figure 3:
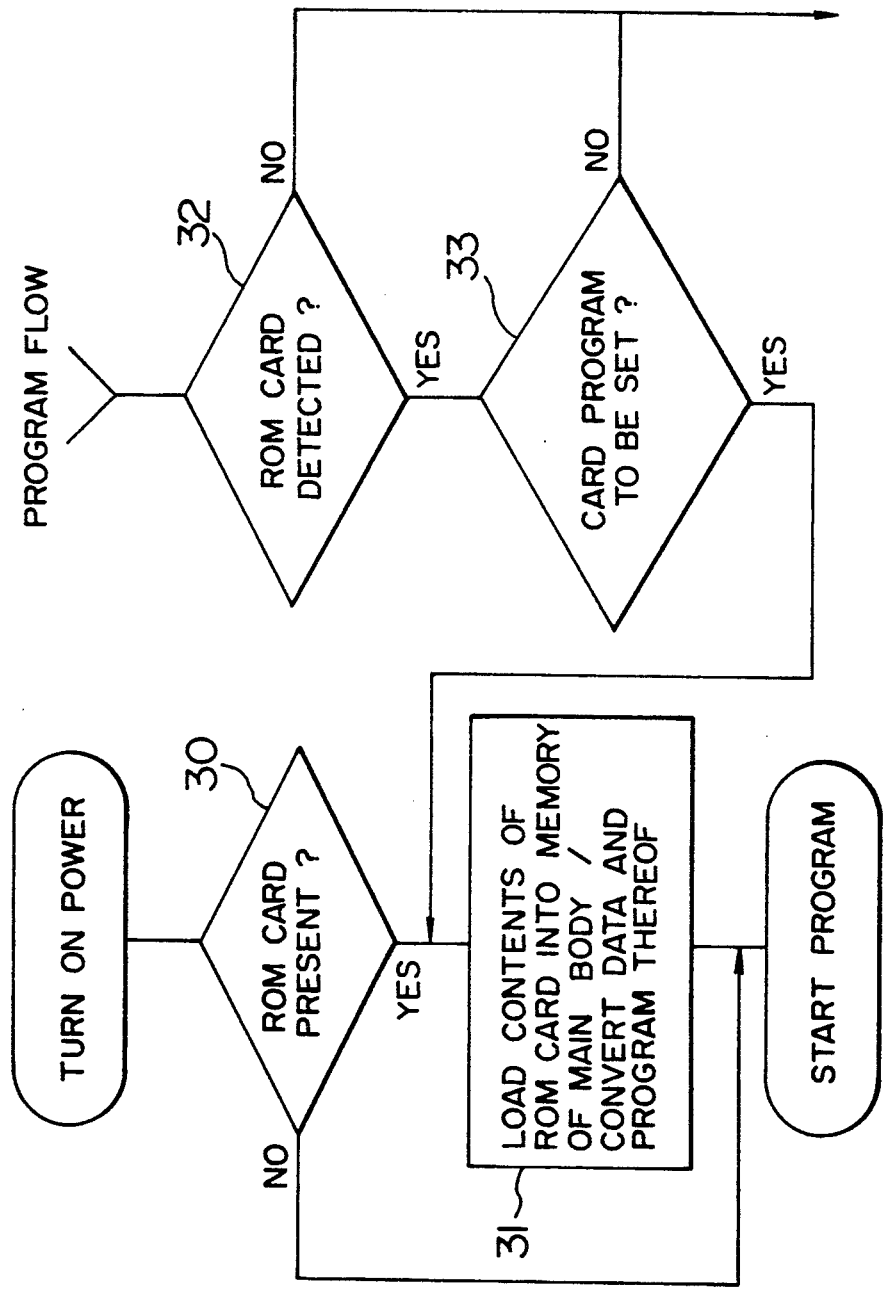
FIG. 3 is a flowchart for explaining a state when a ROM card is to be loaded into the embodiment apparatus.

Referring first to FIG. 1, there is shown a perspective view of an ultrasonic diagnostic apparatus for ophthalmology in accordance with an embodiment of the present invention, which includes a main body 1 having a control circuit, a processing circuit and so on built therein. More specifically, the main body 1 further has power switch 2, a display 3, for indicating diagnosed results thereon, a knob 4 for adjusting the amplifier volume, a connector 5 for connecting a probe 6, a card connector 7 for inserting a ROM or RAM card therein, and a printer 8 for printing measured and diagnosed results on a paper sheet. Also included in the apparatus is keyboard 9 through which an operator controls the main body 1 o enters data on patients into the main body 1.

Shown in FIG. 2 is a block diagram of the entire apparatus. More in detail, the main body 1 incorporates a microcomputer 10 which performs general control of the apparatus. The examiner operates the external keyboard 9 connected to the main body 1 to instruct the microcomputer 10 to execute a control command from the keyboard 9. The microcomputer 10 controls a probe drive 11 according to the received command to cause vibration of a vibrator provided in the probe 6 and to cause transmission of ultrasonic waves to an eyeball to be diagnosed. The reflection echos from various portions of the interior of the eyeball are received at 4 a receiver provided in the probe 6, converted into electrical signals of time series and then sent to the main body 1 (more specifically, to an amplifier 12 provided therein). The diagnosis data sent from the receiver of the probe 6 is amplified by the amplifier 12 and then sent to a sampling/measuring circuit 13 for its processing. The data processed at the sampling-/measuring circuit 13 is further supplied to a waveform/image display circuit 14 to be shown in the display 3 in the form of an A-mode waveform or B-mode image. The data processed at the sampling/measuring circuit 13 is also sent to the microcomputer 10 so that the necessary messages or a graph can be indicated on the display 3 through a letter graphics display circuit 15.

Also connected to the microcomputer 10 is a card interface 16 through which data transfer can be realized between the microcomputer 10 and a memory card 17 inserted in the card connector 7. The memory card 17 refers to a card-sized device having memory incorporated therein. In the present embodiment, the memory card 17 can be a RAM card whose contents can be freely rewritten by the operator, or a ROM card whose contents cannot be rewritten by the operator. The ROM card is used to store therein new programs or data which can be modified or added to. Such modifications or additions include, for example, an IOL or a power formula. In contrast, the RAM card are used to store patient-specific data obtained thorough measurement.

Figure 4:
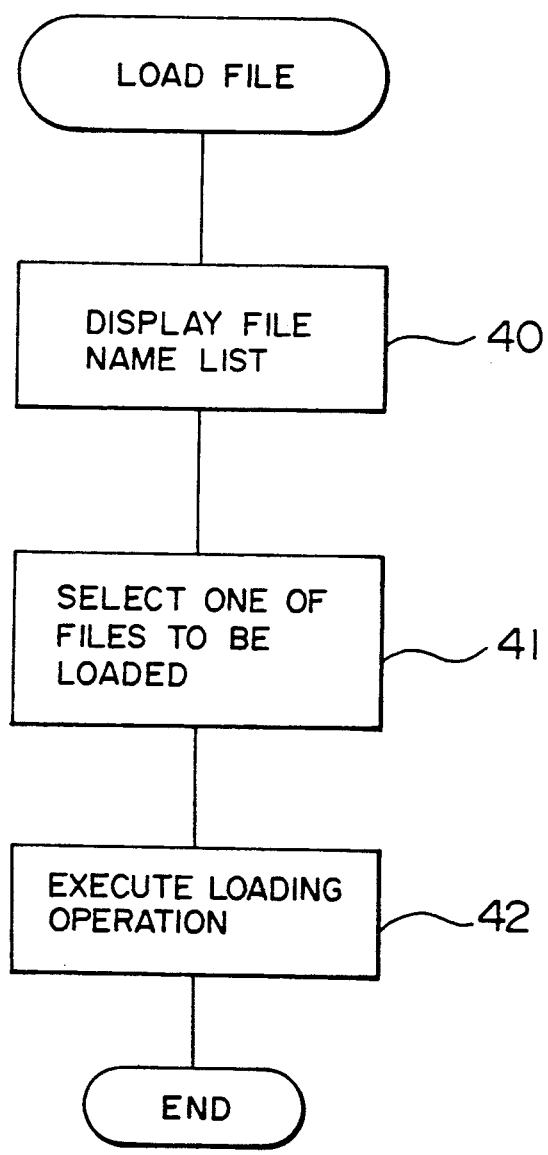
FIG. 4 is a flowchart for explaining a state when a RAM card is to be loaded into the embodiment apparatus.

An explanation will next be made as to data transfer between the memory card 17 and the microcomputer 10 by referring to the flowcharts of FIGS. 3 to 5.

First, a description will be made in connection with the case where the ROM card is used. As shown in FIG. 3, after the power is turned ON, the microcomputer 10 determines whether the ROM card is present or not (step 30). The microcomputer 10, when determining the absence of the ROM card, starts the program built in the main body 1. When determining the presence of the ROM card, the microcomputer 10 causes the loading of the contents of the ROM card into a memory of the main body 1 and the conversion of the program and data of the main body 1 (step 31), and then the microcomputer 10 starts the converted program of the main body 1.

Even during execution of the program, the microcomputer 10 determines whether the ROM card is present or not (step 32). The absence of the ROM card causes the microcomputer 10 to execute the currently running program without any conversion. The presence of the ROM card causes the microcomputer 10 to proceed to a step 33 to judge whether the program of the ROM card is set or not. When determining that the program of the ROM card should not be set, the microcomputer 10 executes the currently running program. When determining that the program of the ROM card should be set, the microcomputer 10 proceeds to the step 31 to load the contents of the ROM card into the memory of the main body 1 and to convert the current program and data of the main body 1. All the contents of the ROM card are loaded into the memory of the main body 1. This is because, after the contents of the ROM card are all loaded and then the ROM card is removed, the RAM can be made ready for its use.

For realizing an ultrasonic diagnostic apparatus for ophthalmology of a simple arrangement at a low cost, the present embodiment is arranged so that, each time the power is turned ON, the ROM card must be inserted into the card connector 7 to load the contents of the ROM card into the memory of the main body 1. Accordingly, it will be readily appreciated that, when it is desired to use a new program or data that has been modified or added to without inserting the ROM card each time the power is turned ON, a back-up circuit in the main body can be provided.

The next explanation will be directed to the use of the RAM card. The RAM card contains data on a plurality of patients in the form of files, each file corresponding to one of the patients. That is, the files respectively correspond to the plurality of patients and have their unique file names for discrimination therebetween. When it is desired to load a particular file, the operator first inserts the RAM card and displays a list of the file names contained in the card (step 40) as shown in FIG. 4. Then the operator selects the desired file name (step 41) and executes its loading operation (step 42). After having read the past data on the target patient from the RAM card in this way, the examiner can immediately conduct a diagnosis based on a new program or data which has modifications or additions already incorporated. The RAM card may also be used, for example, in the following manner. That is, the examiner can conduct only measurements of patients and store the measured results in the RAM card in the morning. In the afternoon, the examiner, after having conducted measurements of out-patients, can read out the data from the RAM card and can collectively diagnose and process the data.

Figure 5:
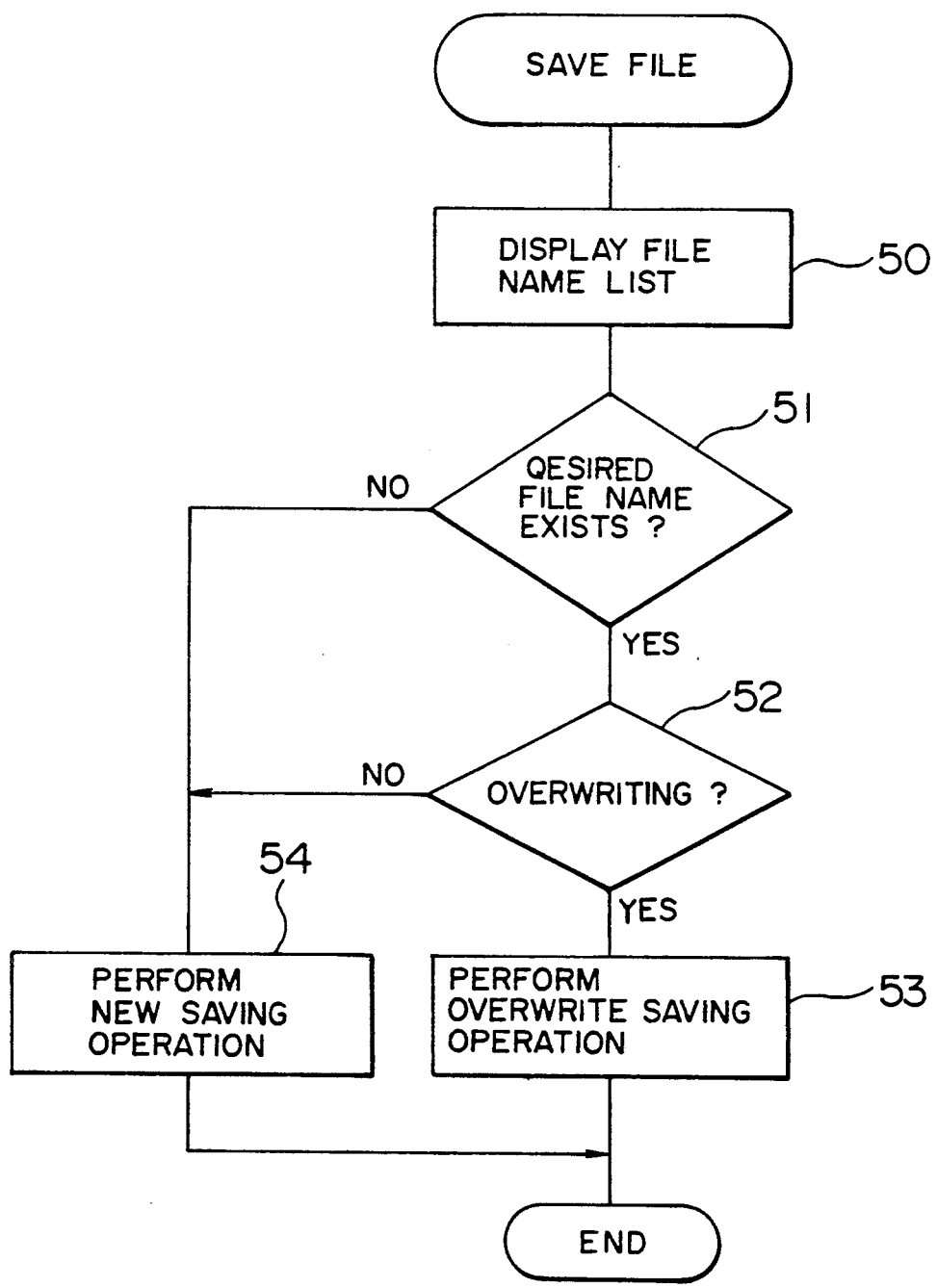
FIG. 5 is a flowchart for explaining the saving operation of the RAM card in the embodiment apparatus.

The saving operation of the stored patient data is carried out according to the flowchart of FIG. 5. First, the operator displays a list of saved file names (step 50) and determines the presence or absence of file names to be saved (step 51). In the absence of a desired file name, control goes to a step 54 where the operator makes a new file name and saves the stored data in the new file. In the presence of the desired file name, control goes to a step 52 to judge whether to overwrite the stored data thereon or not. The determination of a no overwriting operation causes control to go to the step 54 to execute a new saving operation. The determination of an overwriting operation causes control to go to a step 53 to overwrite the stored data thereon and save the new data in the file.

In accordance with the ultrasonic diagnostic apparatus for ophthalmology of the present invention, even if a new processing sequence program is published later, the present apparatus can operate with the new program without the need for any additional provision of a corresponding device or circuit. That is, the present apparatus can accommodate the new program by merely changing the old ROM card to a new one containing the new program. In this way, the present apparatus can always facilitate the use of the latest program and data available.

Further, since the past measured results of patients can be reproduced on the apparatus, a series of measurements that record the progress of patients can be facilitated based on the latest program data.

In addition, since the present apparatus can be efficiently used, the burden imposed on both the examiner and patients can be lightened.

What is claimed is:

1. An ultrasonic diagnostic apparatus for ophthalmology for diagnostic transmitting and receiving of ultrasonic waves and for outputting a plurality of ultrasonic reflection echo images therefrom, said apparatus comprising:

a card connector into and from which a memory card is to be inserted and removed;

a memory card for storing ophthalmalogy data, said memory card being removably connected with said card connector;

a microcomputer electrically connected to said memory card for controlling an ultrasonic probe and for obtaining data based on transmission of ultrasonic waves;

memory means for storing the data of said memory card in said microcomputer, said memory means further comprises means for facilitating insertion of another memory card with data to be read out and/or written into said card connector; and a card interface for data transfer between said memory card and said microcomputer, wherein diagnosis data is obtained based on both the data from said memory card and the data obtained by the microcomputer.

2. An ultrasonic diagnostic apparatus for ophthalmology as set forth in claim 1, wherein the data of said memory card includes a program and processing data necessary for diagnosis.

3. An ultrasonic apparatus for ophthalmology as set froth in claim 1, wherein the data of the memory card includes measurement data specific to individual patients.

4. An ultrasonic diagnostic method for ophthalmology for transmitting and receiving ultrasonic waves and for outputting a plurality of ultrasonic reflection echo images therefrom, said method comprising the steps of:

inserting and removing a memory card into and from a card connector connected to a microcomputer;

transferring data between the memory card and the microcomputer through the card connector and storing the data of the memory card in memory of the microcomputer so as to facilitate inserting another memory card with data to be read out and/or written; and obtaining diagnosis data based on data of the memory card and data of the memory of the microcomputer.

5. An ultrasonic diagnostic method for ophthalmology as set forth in claim 4, wherein the data of the memory card includes a program and processing data necessary for diagnosis.

6. An ultrasonic diagnostic method for ophthalmology as set forth in claim 4, wherein the data of the memory card includes measurement data specific to individual patients.

* * * * *